United States Patent [19]

Dervan et al.

[11] Patent Number: 4,837,312

[45] Date of Patent: * Jun. 6, 1989

[54] CHELATOR-FUNCTIONALIZED NUCLEOSIDES AND NUCLEOTIDES AND METHODS FOR MAKING SAME

[75] Inventors: Peter B. Dervan, South Pasadena; Geoffrey B. Dreyer, Pasadena, both of Calif.

[73] Assignee: California Institute of Technology, Pasadena, Calif.

[*] Notice: The portion of the term of this patent subsequent to Jan. 3, 2006 has been disclaimed.

[21] Appl. No.: 695,214

[22] Filed: Jan. 25, 1985

[51] Int. Cl.⁴ .................. C07H 21/00; C07H 19/00; C07H 17/00; C07H 15/12
[52] U.S. Cl. .............................. 536/27; 536/28; 536/29; 536/23
[58] Field of Search .................. 435/6, 91; 536/27–29

[56] References Cited

U.S. PATENT DOCUMENTS 4,529,796  7/1985  Kang et al. ................ 536/27 X
4,665,184  5/1987  Dervan et al. .............. 530/331 X

OTHER PUBLICATIONS

Bergstrom, D. E. et al., *J. Amer. Chem. Soc.*, vol. 100, No. 26, 1978, pp. 8106–8112.
Hertzberg, R. P. et al., *Biochemistry*, vol. 23, No. 17, 1984, pp. 3934–3945.
Schultz, P. G. et al., *Proc. Natl. Acad. Sci. USA*, vol. 80, 1983, pp. 6834–6837.
Chu, B. C. F. et al., *Nucleic Acids Research*, vol. 11, No. 18, 1983, pp. 6513–6529.

*Primary Examiner*—Johnnie R. Brown
*Assistant Examiner*—Jeremy M. Jay
*Attorney, Agent, or Firm*—Lyon & Lyon

[57] ABSTRACT

Nucleosides and nucleotides functionalized with a metal chelator, and methods of synthesizing such nucleosides and nucleotides are described. These compounds are useful, for example, as constituents of nucleic acid probes for diagnostic and therapeutic purposes.

8 Claims, 1 Drawing Sheet

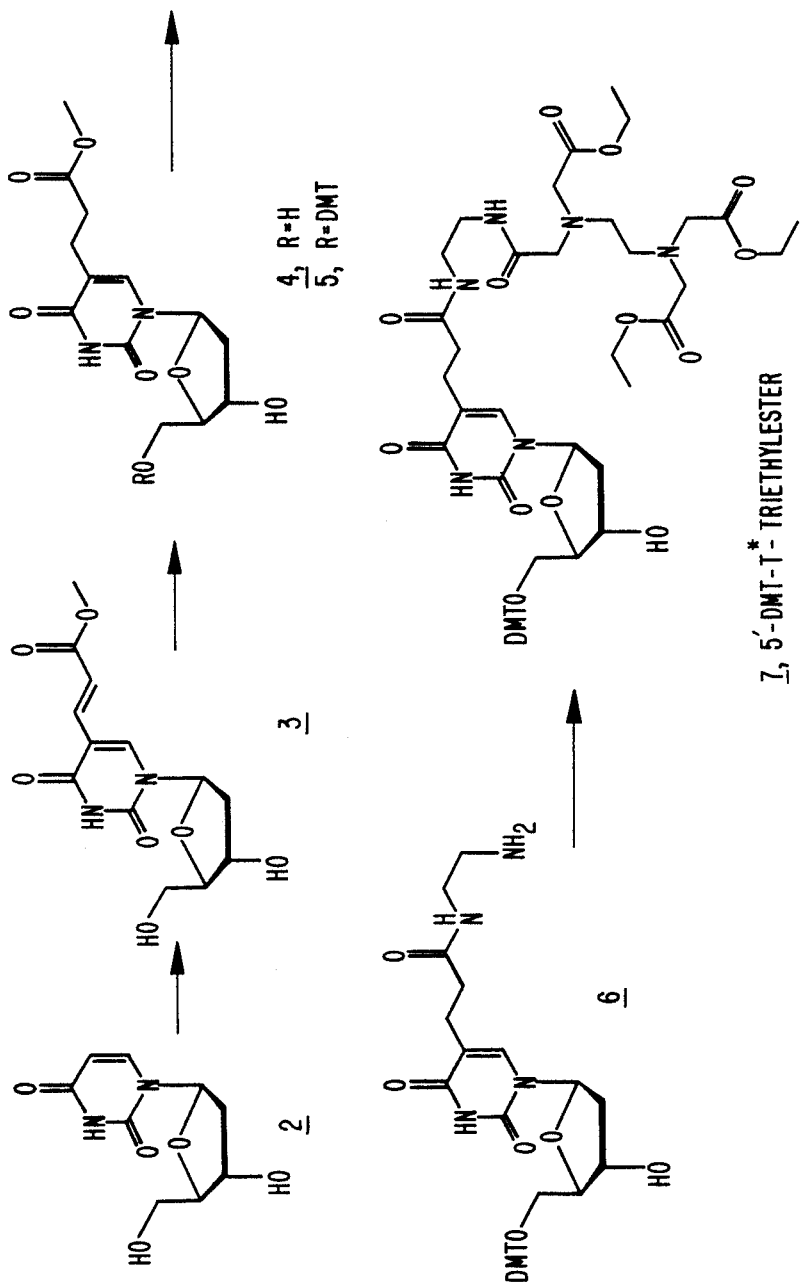

CHELATOR-FUNCTIONALIZED NUCLEOSIDES AND NUCLEOTIDES AND METHODS FOR MAKING SAME

FIELD OF THE INVENTION

This invention relates to novel, chelator-functionalized nucleosides and nucleotides and to methods of synthesizing such nucleosides and nucleotides for use in nucleic acid probes.

BACKGROUND OF THE INVENTION

Nucleosides consist of a nitrogenous base, either a purine or pyrimidine, and a pentose sugar (ribose). When a phosphate group is present at the 5' position of the ribose nucleosides, the structure is called a nucleotide. Nucleotides form the basic units of nucleic acid, and also serve as intermediates in metabolism, in the form of coenzymes.

The bases characteristic of the deoxyribonucleosides which form deoxyribonucleic acid (hereafter DNA) are thymine, cytosine, adenine and guanine. Those characteristic of the ribonucleosides which comprise ribonucleic acid (hereafter RNA) are uracil, cytosine, adenine and guanosine. Other forms of these nucleosides exist, for example deoxyuridine.

DNA and RNA consist of covalently linked chains of deoxynucleotides or ribonucleotides. The links consist of phosphodiester bridges between the 5'-hydroxyl group of one nucleotide and the 3' hydroxyl group of the next. The nitrogenous bases of the linked nucleotides protrude as side chains in DNA and RNA.

Nucleic acid hybridization probes consisting of sequences of deoxyribonucleotides (DNA) or ribonucleotides (RNA) are well-known the art. Typically, to construct a probe, selected target DNA is obtained as a single strand and copies of a portion of the strand are synthesized in the laboratory and labelled using radioactive isotopes, fluorescing molecules or enzymes that react with a substrate to produce a color change. When exposed to complementary strands of target DNA, for example in a sample of tissue fluid taken from a patient, the labelled DNA probe binds to (hybridizes) its complementary DNA sequence. The label on the probe is then detected and the DNA of interest is thus located. The probe may also be used to target RNA sequences. Finally, probes constructed of RNA sequences may be used to hybridize with a single complementary strand of double-helical DNA forming heteroduplexes without necessitating complete denaturation of the double-helical DNA. Thomas et al., *Proc. Nat. Acad. Sci*, 73, p. 2294–2298 (1976); Casey and Davidson, *Nucl. Acids Res.*, 4, p. 1539–1552 (1977). DNA probes are proving useful in locating and identifying selected genes, and in the diagnosis and treatment of infection, genetic disorders and cancer. See, U.S. Pat. No. 4,358,535.

A new era in medical sciences has been generated by the remarkable advances made in the field of genetic engineering. The genetic engineering revolution has been hastened by the discovery of naturally occurring enzymes which cleave double helical deoxyribonucleic acid (hereafter DNA) molecules. These enzymes, called restriction endonucleases, cleave DNA molecules at very specific recognition sites within the DNA polymer. These recognition sites are specific sequences of nucleotides for each restriction enzyme. The sequence-specific cleavage of DNA has found many applications such as DNA sequence determinations, chromosome analyses, gene isolation and recombinant DNA manipulations. Other applications include new and useful diagnostic reagents to detect pathogens and aberrant DNA molecules.

The usefulness of restriction endonucleases has been limited to cleavage of DNA molecules containing the nucleic acid sequences recognized by the limited number of these enzymes. In addition, DNA cleavage by restriction endonucleases is limited to the cleavage of DNA at loci where the sequence recognition site occurs. Thus, endonucleases cannot be used to specifically excise a particular piece of DNA unless, by chance, that piece of DNA contains specific nucleic acid sequences recognized by the limited number of known endonucleases.

The development of synthetic reagents for the sequence specific modification of DNA provides additional tools useful in research, diagnostics and chemotherapeutic strategies. For example, the attachment of a DNA-cleaving moiety such as ethylenediaminetetraacetic acid-iron complex, hereinafter EDTA-Fe(II), to a DNA binding molecule produces an efficient DNA cleaving molecule as described by Hertzberg & Devran, *J. Am. Chem. Soc.* 104, p. 313–315 (1982); *Biochemistry* 23, p. 3934 (1984). Methidiumpropyl-EDTA (hereinafter MPE), which contains the metal been shown to cleave double helical DNA efficiently in a reaction dependent on ferrous ion (FeII) and dioxygen ($O_2$). Addition of reducing agents such as dithiothreitol (hereinafter DTT) increases the efficiency of DNA cleavage, as reported by Hertzberg & Dervan, *J. Am. Chem. Soc.* 104, p. 313–315 (1982); *Biochemistry* 23 p. 3934 (1984). MPE-Fe(II) cleaves DNA in a relatively non-sequence specific manner and with significantly lower sequence specificity than the enzyme DNase I and is thus useful as a research tool in "footprinting" experiments to identify the binding locations of small molecules such as drugs and proteins on native DNA. Van Dyke & Dervan, *Cold Spring Harbor Symp. Quant. Biol.* 47, p. 347–353 (1982); *Biochemistry* 22 p. 2373–2377 (1983); *Nucleic Acids Res.* 11, p. 5555–5567 (1983); *Science* 225 p. 1122, (1984).

Many small molecules important in antibiotic, antiviral and antitumor chemotherapy bind to double helical DNA. Until recently knowledge of the DNA base sequence specificities for these small DNA-binding molecules, such as antibiotics, was limited due to the need to rely on the overall binding affinity of such drugs to homopolymer and copolymer DNAS. The attachment of the cleaving complex EDTA-Fe(II) to antibiotics such as distamycin (hereafter DE) followed by DNA cleavage pattern analyses from Maxam-Gilbert sequencing gels has yielded information on the DNA binding sites and orientation of such drugs on DNA. Hertzerg and Dervan, *J. Am. Chem. Soc.*, 104, p. 313–315 (1982); Taylor et al., *Tetrahedron*, 40, p. 457–465 (1984); *Science*, 225, p. 1122–1127 (1984).

The mechanism of cleavage by EDTA-FeII complexed with synthetic molecules such as methidium or antibiotics such as distamycin is thought to occur by a common mechanism wherein MPE or DE bind in the minor groove of the right-handed DNA helix by hydrophobic and hydrogen bonding interactions and the cleavage most likely involves diffusible hydroxyl radical. Hertzberg and Dervan, *Biochemistry* (in press 1984); *Tetrahedron*, 40, pg. 457–465 (1984).

The above described methods for sequence-specific DNA cleavage have been limited to double-stranded DNA and to those sequences of DNA recognized by antibiotics and DNA intercalators such as methidium. It would provide increased specificity and flexibility with regard to the possible target nucleic acid sequences if sequence-specific cleavage of single stranded nucleic acid and a wider variety of nucleic acid sequences could be accomplished.

SUMMARY OF THE INVENTION

According to this invention there are provided compounds of structure:

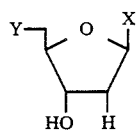

where Y is OW where W is a hydroxy protecting group, and where X comprises a chelator-modified nucleoside base selected from the group consisting of uracil, guanine, adenine, thymine and cytosine; the invention also includes chelator-functionalized nucleotides and methods for making same.

BRIEF DESCRIPTION OF THE DRAWINGS

FIG. 1 illustrates the synthesis of two chelator-functionalized nucleosides (6 and 7 of the drawing).

DETAILED DESCRIPTION OF THE INVENTION

We have synthesized novel nucleosides and nucleotides containing a metal chelator attached to a hydrocarbon tether using a versatile and practical method compatible with known nucleotide synthesis methodology. This method allows the attachment of a metal chelator such as EDTA at various positions in the nucleoside, for example at the 5' carbon atom of the ribose, or the 5, 7, 8 carbon atoms, of the nucleoside base or the 5' or 3' terminal phosphate of polynucleotides or as part of the phosphotriester internucleotide linkage in polynucleotides. The chelator may be attached during synthesis to the nucleosides or nucleotides by a tether consisting of a hydrocarbon amide linkage.

Aliphatic substitution of a metal chelator at the fifth carbon of pyrimidine nucleotide bases can be achieved by palladium mediated olefination reactions as described by Bergstrom, & Ruth, *J. Carbohydrates Nucleosides Nucleotides* 4, p. 257–269 (1977); Bergstrom, & Ogawa, *J. Am. Chem. Soc.* 100, p. 8106–8112 (1978); Heck, *J. Am. Chem. Soc.* 90, p. 5518–5526 (1968); and Langer, Waldrop, & Ward, *Proc. Natl. Acad. Sci.* (U.S.A.) 78(11), p. 6633–6637 (1981). Palladium (II) coupling chemistry has been used to introduce alkyl side chains at carbon five or uridine, deoxyuridine, cytosine and deoxycytosine via the carbon five mercury or halogen derivatives. Langer, Waldrop and Ward, *Proc. Nat. Acad. Sci.* 78(11), p. 6633–6637 (1981).

The metal chelator may also be attached at carbon eight of adenosine and guanosine and deoxyadenosine and deoxyguanosine nucleosides and at carbon seven of deazaadenosine and deazaguanosine nucleosides. The purine bases adenine and guanine can be readily halogenated, and mercurated at carbon eight. Mercuration and halogenation also occur readily at carbon seven of 7-deazapurine nucleoside derivatives. Holmes and Robins, *J. Am. Chem. Soc.*, 86, p. 1242 (1963). Alkyl side chains could be introduced in these halogen and mercuri derivatives by palladium II coupling chemistry. Dale, Livingston and Ward, *Proc. Nat. Acad. Sci.*, 70, p. 2238–2242 (1973). Direct free-alkylation may also be used to introduce alkyl side chains containing a metal chelator at carbon eight of the purine nucleosides. Christenson et al., *Biochemistry* 14(7) p. 1490–1496 (1975).

The metal chelator may also be attached to amino derivatives of nucleosides at the 5' carbon atom of the ribose. Delaney, et al., *J. Carbohydrates, Nucleosides, Nucleotides*, 8(5), p. 445–459 (1981). Alternatively, a metal chelator may be attached to hydrocarbon chains at nitrogen four of cytidine and deoxycytidine nucleosides, using bisulfite-catalyzed transamination to introduce a 3-aminopropyl side chain at carbon four. Draper and Gold, *Biochemistry* 19, p. 1774–1781 (1980) or the metal chelator may be attached at nitrogen four using 4-thiouridine. Smrt. *Neoplasma*, 24, p. 461–466 (1977). A chelator attached to a hydrocarbon tether may also be incorporated at nitrogen six of adenosine and deoxyadenosine, and at nitrogen two of guanosine and deoxyguanosine using reduction amination. Borch, et. al., *J. Am. Chem. Soc.*, 93 p. 2897 (1971).

The tethered metal chelator may be attached to the 3' or 5' terminal phosphate of polynucleotides and nucleic acids using a phosphoamidate linkage, (Chu et. al., *Nucl. Acids Res.*, 11, p. 6513–6528 (1983)), or to an internucleotidyl phosphate of polynucleotides. Asseline et al., *C.R. Acad. Sc. Paris*, 297, p. 369–376 (1983); *Prop. Natl. Acad. Sci* 81, *p.* 3297–3301 (1984). Finally the chelator could be tethered to uridine 3' phosphate and uridine 5' phosphate 6-aminohexyl esters. Smrt, *Coll. Czech. Chem. Commun.*, 44, p. 589–592 (1979).

The metal chelators for use in synthesizing the nucleosides and nucleotides of the present invention may be polyamino carboxylic acid chelator such as ethylenediamine tetraacetic acid (hereafter EDTA), 1,2-diamino-cyclohexane tetraacetic acid (hereafter DCTA), diethylene-triamine pentaacetic acid (hereafter DTPA), ethylenediamine di(-0-hydroxy phenylacetic acid) (hereafter EDDHA) and hydroxyethylene diamine triaacetic acid (hereafter HEEDTA).

The novel nucleosides and nucleotides of this invention may be used in the nucleic acid probes disclosed in co-pending application entitled "NUCLEIC ACID PROBES AND METHODS OF USING SAME" assigned to the same assignee as this application, and filed concurrently herewith, which disclosure is incorporated by reference herein. Such probes are comprised of an acid-cleaving moiety, a metal chelator, such as EDTA-Fe(II), and a polynucleotide sequence complementary to and thus capable of binding a specific nucleic acid sequence. Such probes can provide for specific cleavage of single-stranded (and denatured double-stranded) DNA or RNA at any desired loci utilizing such sequence-specific compositions as nucleic acid probes. In the preferred embodiment, the nucleic acid-cleaving moiety, a metal chelator, is attached to a nucleoside base during synthesis of a novel nucleosides and the so-modified nucleoside is then incorporated into a selected polynucleotide using standard procedures. This polynucleotide containing the chelator-modified nucleoside is complementary to a nucleotide sequence in the DNA or RNA for which a probe is desired. Alternatively, the metal chelator may be attached to a selected nucleotide located within a polynucleotide sequence. In the presence of dioxygen ($O_2$), an appropriate metal ion and a reducing agent, the DNA or RNA-chelator probe affords selective cleavage at its complementary RNA or DNA sequence. The probes of the present invention are not limited to the production of sequence specific cleavage of DNA or RNA but may also be utilized as diagnostic agents when a radiolabelled, fluorescing, or otherwise detectable metal ion is attached to the probe.

The polynucleotide-chelator probes of the present invention for a specific nucleic acid sequence are preferably produced by the incorporation of a novel nucleoside functionalized with a metal chelator such as ethylene-diamine tetraacetic acid (hereafter EDTA). Other polyamino carboxylic metal chelators may be utilized in place of EDTA such as DCTA, DTPA, EDDHA and HEEDTA. The specificity of the probe for the reaction site is prescribed by the nucleotide sequence within which the metal chelator is attached. Nucleosides other than those derived from deoxyuridine such as those derived from the nucleoside bases thymine, cytosine, uracil, adenine and guanine, may be functionalized with the chelator. The EDTA-functionalized nucleoside can then be incorporated into polydeoxynucleotides (DNA) or polynucleotides (RNA) of any desired length and sequence using routine phosphoramidite or phosphotriester procedures.

In addition to providing sequence-specific cleavage of selected DNA or RNA, the probes of the present invention may be used as diagnostic agents for the detection of the presence of DNA or RNA viruses in biological fluids such as blood or urine or in tissue specimens after standard fixation techniques. DNA and RNA viruses such as Cytomegalovirus, hepatitis virus, or measles virus in biological fluids or tissue specimens may be detected after applying standard techniques for dissolving the viral coats, denaturing the viral genome, if the genome is double-stranded, to prepare single-stranded polynucleotides, and hybridizing the single-stranded viral genome with a probe prepared as disclosed in the present application containing a sequence complementary to at least a part of the viral genome. Capture of the double-stranded hybridization product is accomplished by detection of the hybridized product using means appropriate to the properties of the metal ion used. One would detect a radioactive metal by conventional methods used by those in the art for detecting radioactive emissions or detect fluorescing metals using appropriate wave length detectors. For DNA-EDTA Fe(II) probes one would detect cleavage of the DNA or RNA target strand by gel electrophoresis techniques i.e. the appearance of shorter, discrete nucleic acid fragments.

These polynucleotide-chelator probes may also be used to detector specific DNA sequences in tissue specimens. All or part of nucleotide sequences for several oncogenes and several aberrant genes which are associated with specific genetic abnormalities are known. A probe is disclosed in the present application, complementary to at least part of the sequences of an oncogene or an aberrant gene sequence may also be prepared and utilized to detect the presence of these genes in tissue or cell samples. After extraction of the DNA from the specimens by conventional techniques and denaturation procedures to produce single-stranded DNA, one can hybridize the probe prepared as disclosed in the present application and detect the hybridized product by means appropriate to the detection of the metal ion utilized.

The example which follows describes an embodiment wherein novel nucleosides are synthesized from deoxyuridine and functionalized by the metal chelator EDTA.

EXAMPLE 1

For this example, synthesis of and cleavage by the DNA-EDTA probe was performed using the following procedures and reagents. Thin layer chromotography (TLC) was performed with precoated 0.25 mm Silica Gel 60 F-254 TLC plates (EM Reagents). Flash chromatography was performed with EM Reagents Silica Gel 60 (230-400 mesh). Reagent grade chemicals were used without purification unless otherwise stated. Deoxyuridine and dithiothreitol (hereafter DTT) were purchased from Calbiochem. Protected deoxynucleoside phosphoramidites were prepared by procedures as described in the literature. Beaucage, & Caruthers, *Tetrahedron Lett.* 22, p. 1859–1962, (1981). $K_2PdCl_4$, and 10% Pd on C were from Alfa-Ventron. $Fe(NH_4)_2 6H_2O$ was from Baker. Aqueous 5'-[$\alpha-^{32}P$] dATP (3,000 Ci/mmol) was from Amersham, and aqueous 5'-[$\alpha-^{32}P$] ATP (7,000 Ci/mmol) was from ICN. Standard nucleotide triphosphates (NTP's) were from Boehringer Mannheim. All enzymes were from New England Biolabs except bacterial alkaline phosphatase and T4 polynucleotide kinase, which were from Bethesda Research Laboratories. Solutions of $Fe(NH)(SO_4)_2$ and DTT were freshly prepared. Plasmid pBR322 was grown in *E. coli*, strain HB101, and isolated by standard procedures.

IR spectra were recorded on a Shimadzu IR-435 spectrophotometer. UV-visual spectra were recorded on a Beckman Model 25 spectrophotometer. $^1$H NMR spectra were recorded at 500 MHz on a Bruker WM 500 spectrometer using tetramethylslIane (TMS) or sodium 3-(trimethylsilyl)-propane sulfonate (for spectra recorded in $D_2O$) as an internal reference. Chemical shifts are reported in ppm downfield from TMS. Fast atom bombardment (FAB) mass spectra were recorded on a Kratos MS-50 spectrometer at the Midwest Center for Mass Spectrometry at the University of Nebraska, Lincoln. Elemental analyses (Anal.) were performed by Spang Microanalytical, Eagle Harbor, Mich. Gel scans were performed on a Cary 219 spectrophotometer with an Apple microcomputer gel scanning program.

Preparation of a novel
nucleoside—5—DMT-T*-triethylester

The synthesis of 5'-DMT-T*-triethylester is depicted in FIG. I. A DNA-EDTA probe as described fully in the co-pending application "NUCLEIC ACID PROBES AND METHODS OF USING SAME", may be formed by incorporation of this nucleoside which is a protected, EDTA-funtionalized derivative of deoxyuridine into a polydeoxyribonucleotide sequence using standard oligonucleotide synthesis procedures.

(a) Synthesis of Nucleoside 3

2'-Deoxyuridine ("2" of FIG. I) was converted via its 5-chloromercuri derivative to 5-substituted nucleoside 3 ("3" of FIG. I) by a modification of the procedure described in Bergstrom and Ruth, *J. Carbo. Nucleosides Nucleotides* 4, p. 257–269 (1977); and Bergstrom and Ogawa, *J. Am. Soc. Chem.* 100, p. 8106–8112 (1978), using a palladium (II)-mediated coupling reaction with methylacrylate and 5-chloromercuri deoxyuridine. A solution of 2'-deoxyuridine (2.28 g, 10.0 mmol) (2 of FIG. I) and Hg(OAc)$_2$ (3.38 g, 10.6 mmol) in H$_2$O (10 mL) was stirred at 50° C. for 16 hr., after which NaCl (1.5 g, 25 mmol) in H$_2$O (10 mL) was added with stirring. The mixture was concentrated to dryness by rotary evaporation. The remaining white solid was rinsed with methanol (5×20 mL) and ether (25 mL) in a fritted glass funnel, then dried, yielding the mercurinucleoside (4.58 g, 9.89 mmol; 99% yield): mp 218°–219° C. (decomposition). To a mixture of 5-chloromercuri-2'deoxyuridine (1.85 g, 4.00 mmol), methyl acrylate (1.50 mL, 20.00 mmol; freshly distilled) and methanol (50 mL) was added a solution of K$_2$PdCl$_4$ (1.30 g, 4.00 mmol) in H$_2$O (13 mL). After 3.5 hr. stirring the mixture was treated with H$_2$S for 2 min, then filtered through Celite (Sigma). The filtrate was concentrated to dryness and purified by flash chromatography (MeOH-EtPOAc 15:85) followed by recrystallization (MeOH-EtOAc 15:85), to give nucleoside 3 (FIG. I) (748 mg, 2.40 mmol; 60% yield) with the following characteristics: mp 169°–170° C., 1H NMR (D$_2$O): δ 8.25 (1H, s, H$_6$), 7.37 (1H, d, J=15.9 Hz), 6.7 (1H, d, J=15.9 Hz), 6.24 (1H, t, H$_1$'), 4.48 (1H, m, H$_3$'), 4.07 (1H, m, H$_4$'), 3.90–3.80(2H, m, H$_5$'), 3.77 (3H, s, OCH$_3$), 2.48-2-37 (2H, m, H$_2$'). IR (KBr): 3440, 3240, 3080, 2960, 1730, 1670, 1620, 1520, 1440, 1290, 1100 cm$^{-1}$. UV (H$_2$O): 302 nm (19,000). MS: (pos. ion FAB) m/z 313 (M++1, 35), 197 (100), 165 (85 ), 117 (79); (neg.ion FAB) m/z 311 (M+$^{-1}$, 48), 195 (100). Anal. calc'd for C$_{13}$H$_{16}$N$_2$O$_7$: C, 50.00; H, 5.16; N, 8.97. Found: C, 49.84; H, 5.25; N, 8.77. TLC (MeOH-EtOAc 15:85): Rf=0.46.

Of several olefinic substrates tested, the Pd(II)-mediated coupling reaction of methyl acrylate and 5-chloromercurideoxyuridine proved most satisfactory in producing Nucleoside 3 in good yield.

(b) Synthesis of Nucleoside 4. Compound 3 was then hydrogenated to selectively reduce the exocyclic bond to yield Nucleoside 4 (FIG. I). A solution of nucleoside 3 (780 mg, 2.50 mmol) in MeOH (75 mL) was shaken with 10% Pd on C (117 mg) under H$_2$(50 psi) for 58 h, using a Parr Apparatus. Filtration and evaporation afforded analytically pure nucleoside 4 (748 mg, 2.38 mmol; 95% yield) (4 of FIG. I) with the following characteristics: 'H NMR (D$_2$O): 7.72 (1H, s, H$_6$), 6.28 (1H, t, H$_1$'), 4.47 (1H, m, H$_3$'), 4.03 (1H, m, H$_4$'), 3.86–3.75 (2H, m, H$_5$'), 3.68 (3H, s, OCH$_3$), 2.62 (4H, m), 2.42–2.30 (2H, m, H$_2$'). IR (film): 3400, 3040, 2930, 1690, 1465, 1440, 1275, 1090, 1050 cm$^{-1}$. UV (H$_2$O): 268 nm (9,300). MS: (pos. ion FAB) m/z 315 (M++1, 27,), 199 (100), 167 (63), 117 (38); (neg. ion FAB) m/z 313 (M+−1, 72), 197 (100). Anal. calc'd. for C$_{13}$H$_{18}$N$_2$O$_7$: C, 49.68; H, 5.77; N, 8.91. Found: C, 49.35; H, 5.96; N, 8.51. TLC (MeOH-EtOAc 15:85): Rf=0.41.

(c) Synthesis of Nucleoside 5. The 5'-hydroxy group of 4 was protected with dimethoxytritylchloride (DMTC) to yield nucleoside 5 after the procedures of Schaller et al., J. Am. Chem. Soc. 85, 3821-27 (1963). A solution of nucleoside 4(200 mg, 0.64 mmol) and 4,4'-dimethoxytrityl chloride (238 mg, 0.70 mmol) in dry pyridine (1.0 mL) was stirred for 4 h under Ar. Methanol (0.5 mL) was added and after 30 min the mixture was concentrated under vacuum to a gum, which was dissolved in CH$_2$Cl$_2$(5 mL), rinsed with H$_2$O (2×5 mL) and reconcentrated. Flash chromatography (MeOH-CH$_2$Cl$_2$ 5:95) provided nucleoside 5 (320 mg, 0.52 mmol; 81% yield) (5 of FIG. I) with the following characteristics: $^1$H NMR (CDCl$_3$): δ 8.13 (1H, s), 7.49 (1H, s, H$_6$) 7.39 (2H, d), 7.30–7.22 (7H), 6.82 (4H, d), 6.33 (1H, t, H$_1$'), 4.53 (1H, m, H$_3$'), 4.01 (1H, m, H$_4$'), 3.78 (6H, s, OCH$_3$), 3.57 (3H, s, OCH$_3$), 3.42 (2H, m, H$_5$'), 2.36 (2H, m, H$_2$'), 2.30–2.21 (4H, m), 1.94 (1H, d). MS: (pos. ion FAB) m/z 617 (M++1, 24), 605 (31), 375 (78), 303 (100), 199 (45), 167 (33); (neg. ion FAB) m/z 615 (M+−1, 34), 273 (15), 197 (100), 183 (53). Anal. calcd. for C$_{34}$H$_{36}$N$_2$O$_9$: C, 66.22; H, 5.89; N, 4.54. Found: C, 66.62; H, 5.99; N, 4.66. TLC (MeOH-CH$_2$Cl$_2$ 5:95): Rf=0.40.

(d) Synthesis of Nucleoside 6. A solution of nucleoside 5 (320 mg, 0.519 mmol) in freshly distilled excess ethylenediamine (5.0 mL) was stirred under AR for 57 h, at which point silica TLC indicated complete conversion of 5 to a single product (Rf=0.44) in conc. aq. NH$_3$-MeOH 5:95). The mixture was reduced under vacuum to a gum, redissolved in dioxane, then lyophilized.

(e) Synthesis of Nucleoside 7. The resulting powder, nucleoside 6 ("6" of FIG. I) was stirred with EDTA-triethylester-N-hydroxysuccinimide ester (1.4 mmol; prepared as reported in Taylor, et al., Tetrahedron 40, 457-465 (1980) in dioxane (15 mL) under Ar for 1 h. The mixture was then stirred with ethanol (5 mL) for 15 min, concentrated, redissolved in CH$_2$Cl$_2$ (15 mL), rinsed with H$_2$O (3×10 mL) and reconcentrated. Flash chromatography (eluting with 100 mL 5% EtOH in CH$_2$Cl$_2$ then 150 mL 15% EtOH in CH$_2$Cl$_2$) afforded the protected base, 5'DMT-T-triethylester (262 mg, 0.257 mmol; 55% yield) (7 of FIG. I) as a brittle foam with the following characteristics: $^1$H NMr (CDCl$_3$): δ 9.67 (1H, bs), 8.44 (1H, m), 7.47 (1H, s, H$_6$), 7.41 (2H, d), 7.32–7.21 (7H), 6.88 (1H, m), 6.84 (4H, d), 6.36 (1H, t, H$_1$'), 4.48 (1H, m. H$_3$'), 4.13 (6H, m, OCH$_2$CH$_3$), 4.05 (1H, m, H$_4$'), 3.78 (6H, s, OCH$_3$), 3.70 (2H, s), 3.53 (4H, s), 3.39–3.28 (8H), 2.78 (4H, dm), 2.45–2.20 (7H), 1.24 (9H, t, OCH$_2$CH$_3$). IR (CCl$_4$): 3300, 2990, 2920, 1740, 1675, 1605, 1500, 1460, 1440, 1370, 1300, 1270, 1250, 1185, 1135, 1030 cm$^{-1}$. UV(CHCl$_3$): 242 nm (15,000), 270 nm (9,600). MS: (pos. ion FAB) m/z 1003 (M++1, 13), 919 (32), 777 (39), 701 (6), 461 (100), 303 (95), 216 (83); neg. ion (FAB) m/z 1001 (M+−1, 3), 653 (21), 566 (98), 520 (33), 413 (74), 367 (20), 273 (39), 196 (69), 137 (100). Exact mass (pos. ion FAB), calc'd for C$_{51}$H$_{67}$N$_6$O$_{15}$ (M+H)+: 1003.4663. Found: 1003.4648. TLC (EtOH-CHCl$_2$ 1:10): Rf=0.50.

The EDTA-derivatized, protected nucleoside 5'-DMT-T*-triethylester (7), prepared in three steps from nucleoside 3, is a suitable monomer for standard phosphoramidite oligonucleotide synthesis procedures and gives excellent coupling efficiencies. The chelator-functionalized nucleoside is de-protected by hydrolysis after incorporation into polynucleotide sequences for use as a nucleic acid probe.

The chelator-functionalized nucleosides and nucleotides of this invention are not limited to use in chelator-probes for sequence-specific cleavage of DNA or RNA, but may also prove useful as chemotherapeutic agents.

It is understood that various other modifications will be apparent to and can readily be made by those skilled in the art without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

What is claimed is:

1. A compound of structure:

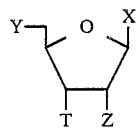

where Z is hydrogen or hydroxy; Y is NHR$_1$, W where w is a hydroxyl protecting group or

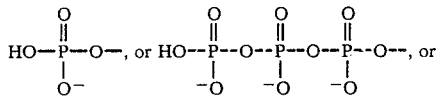

T is hydrogen or hydroxyl or

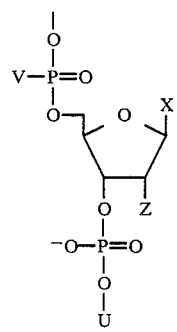

where
Q is OR$_1$, R$_1$ or NHR$_1$, or

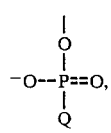

where V is OR$_1$, R$_1$ or NHR$_1$ and where U is a polyribonucleotide or polydeoxyribonucleotide sequence;

and where X is a nucleoside base selected from the group consisting of

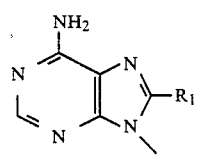
(a)

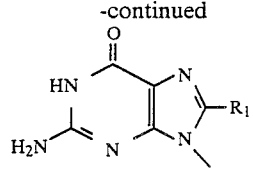
(b)

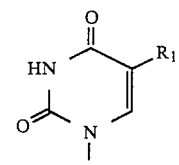
(c)

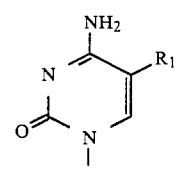
(d)

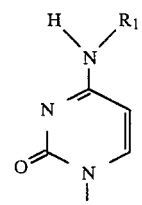
(e)

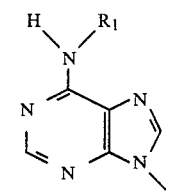
(f)

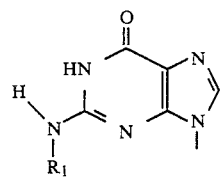
(g)

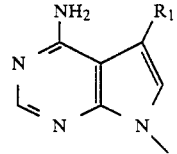
(h)

and

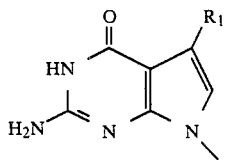
(i)

where R$_1$ is a thethered metal chelator said metal capable of reducing dioxygen; provided, however, that when Y is

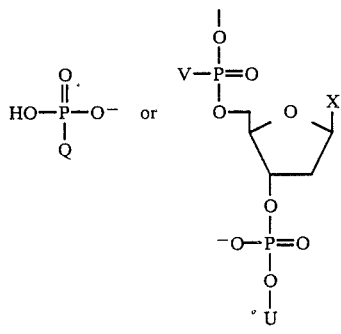

or NHR₁, X is a nucleoside base selected from the group consisting of tethered metal chelator functionalized nucleoside bases guanine, adenine, cytosine, uracil and thymine, provided that when X is thymine, T is hydrogen; and provided that when T is

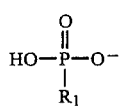

X is a nucleoside base selected from the group consisting of tethered metal chelator functionalized nucleoside bases guanine, adenine, cytosine, uracil and thymine.

2. A compound of structure

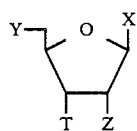

where Z is hydrogen or hydroxyl; Y is hydroxyl or W where W is a hydroxyl-protecting group; T is hydroxyl and X is a nucleoside base selected from the group consisting of

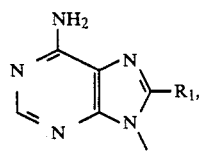 (a)

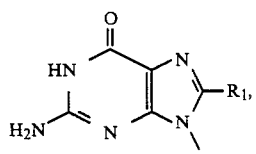 (b)

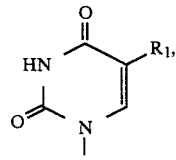 (c)

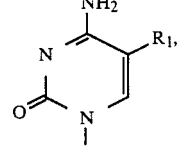 (d)

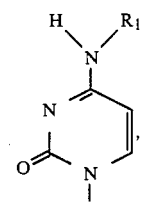 (e)

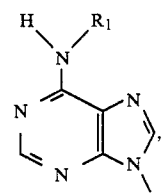 (f)

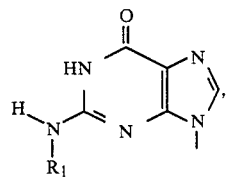 (g)

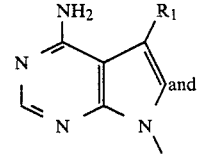 (h)

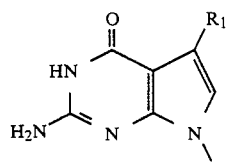 (i)

and where R₁ is a tethered metal chelator said metal capable of reducing dioxygen.

3. The compound according to claim 1 or 2 wherein the hydroxyl protecting group is dimethoxytrityl chloride.

4. The compound according to claim 1 or 2 wherein said tether is a hydrocarbon-amide linkage and said metal chelator is a polyamino carboxylic acid chelator.

5. The compound according to claim 4 wherein said tether is the structure:

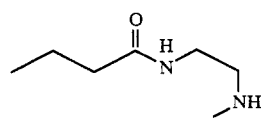

and said chelator is EDTA.

6. The compound according to claim 4 wherein the metal chelator is selected from the group consisting of EDTA, DCTA, DTPA, EDDHA and HEEDTA.
7. The chelator-functionalized nucleoside of structure:
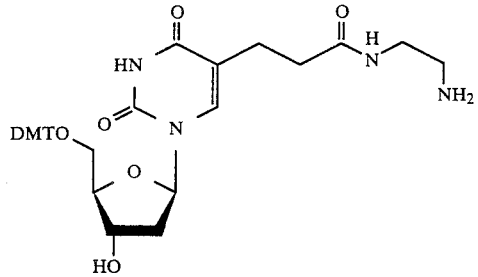
8. The chelator-functionalized nucleoside of structure:
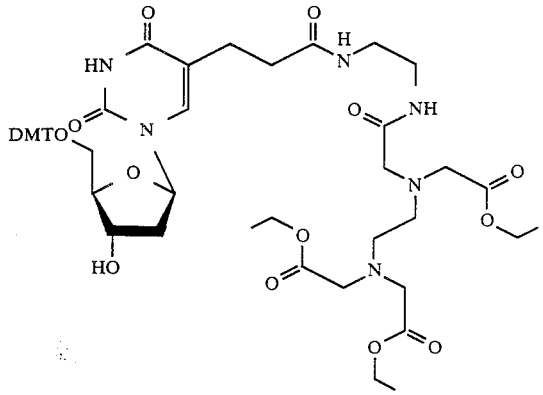
* * * * *